US012714527B2

(12) United States Patent
Oguri

(10) Patent No.: US 12,714,527 B2
(45) Date of Patent: Aug. 25, 2026

(54) DEVICE FOR FINE WORK

(71) Applicant: F.MED CO., LTD., Fukuoka (JP)

(72) Inventor: Susumu Oguri, Fukuoka (JP)

(73) Assignee: F.MED CO., LTD., Fukuoka (JP)

( * ) Notice: Subject to any disclaimer, the term of this patent is extended or adjusted under 35 U.S.C. 154(b) by 196 days.

(21) Appl. No.: 18/682,703

(22) PCT Filed: Aug. 16, 2021

(86) PCT No.: PCT/JP2021/029865

§ 371 (c)(1),
(2) Date: Feb. 9, 2024

(87) PCT Pub. No.: WO2023/021541

PCT Pub. Date: Feb. 23, 2023

(65) Prior Publication Data

US 2024/0358464 A1 Oct. 31, 2024

(51) Int. Cl.
*A61B 34/00* (2016.01)
*A61B 17/29* (2006.01)
(Continued)

(52) U.S. Cl.
CPC .......... *A61B 34/72* (2016.02); *A61B 17/2909* (2013.01); *A61B 34/73* (2016.02);
(Continued)

(58) Field of Classification Search
CPC ..... A61B 34/72; A61B 17/2909; A61B 34/73; A61B 34/30; A61B 2034/304;
(Continued)

(56) References Cited

U.S. PATENT DOCUMENTS 4,979,949 A * 12/1990 Matsen, III ............ A61G 13/12 606/88
5,086,401 A * 2/1992 Glassman ................. A61F 2/46 606/88

(Continued)

FOREIGN PATENT DOCUMENTS

CN 106456265 A * 2/2017 ............ B25J 9/1689
CN 111839741 A 10/2020

(Continued)

OTHER PUBLICATIONS

"Highly precise master-slave robot system for super micro surgery;" Baek et al., 2010 3rd IEEE RAS & EMBS International Conference on Biomedical Robotics and Biomechatronics (2010, pp. 740-745); Sep. 1, 2010. (Year: 2010).*

(Continued)

*Primary Examiner* — Khoi H Tran
*Assistant Examiner* — Jorge O Peche
(74) *Attorney, Agent, or Firm* — Oliff PLC

(57) ABSTRACT

An operating range for fine work while suppressing, as much as possible, variations of the position at which the fine work is performed. A control unit of a fine work device: accepts input of the movement of a position of a tip of a fine work manipulator, the position being a fine-work operating position; calculates, with the operating position serving as a target position, driving amounts for the fine work manipulator and a robot unit, and controls operations of the fine work manipulator and the robot unit on the basis of the driving amounts.

16 Claims, 15 Drawing Sheets

(51) Int. Cl.
*B25J 9/12* (2006.01)
*B25J 13/00* (2006.01)
*A61B 34/30* (2016.01)

(52) U.S. Cl.
CPC ................. *B25J 9/12* (2013.01); *B25J 13/00* (2013.01); *A61B 34/30* (2016.02)

(58) Field of Classification Search
CPC ... A61B 34/37; B25J 9/12; B25J 13/00; B25J 9/0042; B25J 9/1015; B25J 9/1689; G05B 2219/40195
See application file for complete search history.

(56) References Cited

U.S. PATENT DOCUMENTS 5,410,638 A * 4/1995 Colgate .................. A61B 34/70 700/262
5,784,542 A * 7/1998 Ohm ...................... A61B 34/35 901/34
5,855,583 A * 1/1999 Wang ..................... A61B 34/35 606/139
5,952,796 A * 9/1999 Colgate .................. B25J 9/1689 318/1
5,976,156 A * 11/1999 Taylor .................... A61B 34/20 606/130
6,063,095 A * 5/2000 Wang ..................... A61B 34/37 606/139
6,132,368 A * 10/2000 Cooper .................. A61B 34/76 606/1
6,206,903 B1 * 3/2001 Ramans ................. A61B 17/29 606/205
6,223,100 B1 * 4/2001 Green .................. H04N 13/296 348/E13.016
6,246,200 B1 * 6/2001 Blumenkranz ........ A61B 34/70 318/568.25
6,330,837 B1 * 12/2001 Charles ................ B25J 17/0266 901/29
6,364,888 B1 * 4/2002 Niemeyer .............. A61B 34/37 348/E13.016
6,398,726 B1 * 6/2002 Ramans ................. A61B 34/71 600/235
6,424,885 B1 * 7/2002 Niemeyer .............. A61B 34/77 600/109
6,436,107 B1 * 8/2002 Wang ..................... A61B 34/30 606/139
6,468,265 B1 * 10/2002 Evans .................... A61B 34/32 606/1
6,491,691 B1 * 12/2002 Morley .................. A61B 34/71 606/49
6,493,608 B1 * 12/2002 Niemeyer .............. A61B 34/70 700/255
6,565,554 B1 * 5/2003 Niemeyer .............. A61B 34/37 606/1
6,645,196 B1 * 11/2003 Nixon .................... A61B 34/37 606/1
6,699,177 B1 * 3/2004 Wang ..................... A61B 34/77 600/102
6,714,839 B2 * 3/2004 Salisbury, Jr. ......... A61B 34/30 901/14
6,786,896 B1 * 9/2004 Madhani ................ A61B 34/30 606/1
7,035,716 B2 * 4/2006 Harris .................... A61B 34/76 600/102
7,206,627 B2 * 4/2007 Abovitz ................. A61B 34/74 600/407
7,331,967 B2 * 2/2008 Lee ........................ A61B 34/37 600/407
7,497,863 B2 * 3/2009 Solar ...................... A61B 90/11 606/130
7,559,935 B2 * 7/2009 Solar ...................... A61B 90/11 606/130
7,594,912 B2 * 9/2009 Cooper .................. A61B 34/30 606/1
7,607,440 B2 * 10/2009 Coste-Maniere ...... A61B 34/35 600/407
7,666,191 B2 * 2/2010 Orban, III .............. A61B 46/10 606/1
7,741,802 B2 * 6/2010 Prisco .................... B25J 9/1689 318/632
7,831,292 B2 * 11/2010 Quaid .................... A61B 34/37 345/157
7,892,243 B2 * 2/2011 Stuart .................... A61B 34/77 606/130
7,963,913 B2 * 6/2011 Devengenzo .......... A61B 34/71 901/41
8,010,180 B2 * 8/2011 Quaid .................... A61B 34/71 600/426
8,062,288 B2 * 11/2011 Cooper .................. A61B 34/37 606/1
8,498,744 B2 * 7/2013 Odermatt ............... B25J 9/1628 701/472
8,554,368 B2 * 10/2013 Fielding ................. B25J 9/1689 700/251
8,620,473 B2 * 12/2013 Diolaiti ............. A61B 1/00087 600/407
8,644,988 B2 * 2/2014 Prisco .................... A61B 34/71 604/528
8,749,190 B2 * 6/2014 Nowlin .................. A61B 34/37 318/560
8,753,346 B2 * 6/2014 Suarez ................... A61B 90/03 606/81
8,911,429 B2 * 12/2014 Olds ...................... A61B 90/00 606/1
8,996,169 B2 * 3/2015 Lightcap ................ A61B 34/10 700/250
9,008,757 B2 * 4/2015 Wu ........................ A61B 34/20 600/407
9,060,794 B2 * 6/2015 Kang ..................... A61B 34/30
9,060,796 B2 * 6/2015 Seo ........................ A61B 34/77
9,119,638 B2 * 9/2015 Schwarz ............ A61B 17/1626
9,119,655 B2 * 9/2015 Bowling ................ A61B 34/10
9,161,760 B2 * 10/2015 Suarez ............... A61B 17/1622
9,399,298 B2 * 7/2016 Kang ..................... B25J 9/0042
9,554,827 B2 * 1/2017 Omori ................ A61B 17/4241
9,622,823 B2 * 4/2017 Bozung ................... A61F 11/00
9,820,818 B2 * 11/2017 Malackowski ........ A61B 34/20
9,937,014 B2 * 4/2018 Bowling ................ A61B 34/32
10,111,678 B2 * 10/2018 Jinno ..................... A61B 34/37
10,117,713 B2 * 11/2018 Moctezuma de la Barrera .......... B25J 9/1671
10,123,844 B2 * 11/2018 Nowlin .................. A61B 34/35
10,188,472 B2 * 1/2019 Diolaiti .............. A61B 1/00087
10,327,849 B2 * 6/2019 Post ....................... A61B 34/10
10,368,878 B2 * 8/2019 Lavallee .............. A61B 17/154
10,410,746 B2 * 9/2019 Moctezuma de la Barrera .......... G16H 40/40
10,426,560 B2 * 10/2019 Bowling .................. B25J 13/00
10,463,440 B2 * 11/2019 Bowling ................ A61B 34/74
10,483,881 B2 * 11/2019 Liao .......................... H02P 6/14
10,492,875 B2 * 12/2019 Janik ...................... A61B 34/32
10,568,640 B2 * 2/2020 Bozung .............. A61B 17/1617
10,660,711 B2 * 5/2020 Moctezuma de la Barrera .......... A61B 34/20
10,660,715 B2 * 5/2020 Dozeman ............... B25J 9/1694
10,687,905 B2 * 6/2020 Kostrzewski .......... A61B 34/30
10,751,051 B2 * 8/2020 Weir ...................... A61B 34/76
10,828,786 B2 * 11/2020 Shoham ............... B25J 17/0216
11,045,958 B2 * 6/2021 Bowling .................. B25J 9/161
11,173,000 B2 * 11/2021 Bono ..................... A61B 34/25
11,369,438 B2 * 6/2022 Malackowski ........ A61B 34/20
11,529,738 B2 * 12/2022 Ng ............................ G06T 7/73
11,553,938 B2 * 1/2023 Allen, IV ............... A61B 34/30
11,627,979 B2 * 4/2023 Keppler ............... A61B 17/157 606/53
11,633,248 B2 * 4/2023 Gilhooley .............. A61B 34/30 606/130
11,666,318 B2 * 6/2023 Otto ........................ G01L 5/226 606/90

(56) References Cited

U.S. PATENT DOCUMENTS

| | | | | |
|---|---|---|---|---|
| 11,684,374 | B2 * | 6/2023 | Kang | A61B 17/14 606/82 |
| 11,931,122 | B2 * | 3/2024 | Nowlin | A61B 34/35 |
| 12,097,002 | B2 * | 9/2024 | Diolaiti | A61B 90/361 |
| 12,161,437 | B2 * | 12/2024 | Tojo | B25J 9/0087 |
| 12,329,461 | B2 * | 6/2025 | Kuznik | A61B 34/32 |
| 12,558,107 | B2 * | 2/2026 | Bozung | A61B 17/1622 |
| 2002/0082612 | A1 * | 6/2002 | Moll | G16H 40/63 606/130 |
| 2003/0233102 | A1 * | 12/2003 | Nakamura | A61B 34/30 606/130 |
| 2004/0176751 | A1 * | 9/2004 | Weitzner | A61B 34/32 606/1 |
| 2005/0027397 | A1 * | 2/2005 | Niemeyer | A61B 34/37 700/245 |
| 2005/0107680 | A1 * | 5/2005 | Kopf | A61B 7/04 600/407 |
| 2005/0225278 | A1 * | 10/2005 | Ban | B25J 9/1692 318/568.11 |
| 2007/0142968 | A1 * | 6/2007 | Prisco | A61B 1/00193 700/264 |
| 2008/0065102 | A1 * | 3/2008 | Cooper | A61B 17/00234 606/130 |
| 2009/0326324 | A1 * | 12/2009 | Munoz Martinez | A61B 34/30 901/30 |
| 2010/0268249 | A1 * | 10/2010 | Stuart | A61B 34/70 606/130 |
| 2010/0274087 | A1 * | 10/2010 | Diolaiti | A61B 34/30 600/407 |
| 2011/0315413 | A1 * | 12/2011 | Fisher | B25F 3/00 279/144 |
| 2012/0059390 | A1 * | 3/2012 | Mintz | A61B 34/74 606/130 |
| 2012/0078053 | A1 * | 3/2012 | Phee | A61B 34/77 600/139 |
| 2013/0253533 | A1 * | 9/2013 | Bartol | A61B 34/30 606/130 |
| 2014/0088612 | A1 * | 3/2014 | Bartol | A61B 5/6852 606/130 |
| 2015/0157191 | A1 * | 6/2015 | Phee | A61B 34/74 600/106 |
| 2016/0361122 | A1 | 12/2016 | Seeber | |
| 2017/0086931 | A1 * | 3/2017 | Auld | A61B 34/37 |
| 2017/0202629 | A1 * | 7/2017 | Maillet | A61B 34/20 |
| 2018/0078439 | A1 * | 3/2018 | Cagle | A61B 34/70 |
| 2018/0200010 | A1 * | 7/2018 | Hares | A61B 34/30 |
| 2018/0353252 | A1 * | 12/2018 | Chassot | A61B 34/37 |
| 2019/0000576 | A1 * | 1/2019 | Mintz | A61B 90/50 |
| 2019/0133704 | A1 * | 5/2019 | Hiratsuka | A61B 34/37 |
| 2019/0160650 | A1 * | 5/2019 | Oguri | A61B 34/30 |
| 2019/0239972 | A1 * | 8/2019 | Chassot | A61B 34/37 |
| 2019/0328468 | A1 * | 10/2019 | Schena | A61B 34/30 |
| 2019/0328470 | A1 * | 10/2019 | Tojo | A61B 34/25 |
| 2019/0350662 | A1 * | 11/2019 | Huang | A61B 34/74 |
| 2019/0365391 | A1 * | 12/2019 | Nikou | A61F 2/38 |
| 2019/0388099 | A1 * | 12/2019 | Zuhars | A61B 34/10 |
| 2020/0069373 | A1 * | 3/2020 | Yu | A61B 34/10 |
| 2020/0146763 | A1 * | 5/2020 | Schena | A61B 34/37 |
| 2020/0261169 | A1 * | 8/2020 | Miller | A61B 34/30 |
| 2020/0397520 | A1 * | 12/2020 | Penny | A61B 90/361 |
| 2020/0405425 | A1 * | 12/2020 | Shelton, IV | A61B 34/20 |
| 2021/0059780 | A1 * | 3/2021 | Sutherland | A61B 34/74 |
| 2021/0068845 | A1 * | 3/2021 | Schers | A61B 17/02 |
| 2021/0330407 | A1 * | 10/2021 | Chassot | A61B 18/1442 |
| 2021/0369359 | A1 | 12/2021 | Blanckaert et al. | |
| 2022/0061938 | A1 * | 3/2022 | Lee | A61B 34/25 |
| 2022/0233251 | A1 * | 7/2022 | Bowling | A61B 34/20 |
| 2022/0273396 | A1 * | 9/2022 | Bozung | A61B 17/142 |
| 2023/0255701 | A1 * | 8/2023 | Post | A61B 34/30 606/82 |
| 2024/0358464 | A1 * | 10/2024 | Oguri | A61B 34/73 |
| 2025/0041006 | A1 * | 2/2025 | Suzuki | A61B 34/37 |
| 2025/0099113 | A1 * | 3/2025 | Bozung | A61B 17/1622 |
| 2025/0221782 | A1 * | 7/2025 | Dozeman | A61B 17/14 |

FOREIGN PATENT DOCUMENTS

| | | | | |
|---|---|---|---|---|
| DE | 102014101912 | A1 * | 8/2014 | B25J 9/0051 |
| EP | 1584426 | A1 * | 10/2005 | B25J 9/1692 |
| EP | 3372350 | A1 * | 9/2018 | B25J 3/04 |
| EP | 3 789 164 | A1 | 3/2021 | |
| EP | 4 252 969 | A1 | 10/2023 | |
| JP | 2017-000722 | A | 1/2017 | |
| JP | 2017-087322 | A | 5/2017 | |
| JP | 6559691 | B2 * | 8/2019 | A61B 34/30 |
| JP | 6817607 | B2 * | 1/2021 | B25J 3/04 |
| JP | 7481427 | B2 * | 5/2024 | B25J 19/023 |
| WO | 2017/064301 | A1 | 4/2017 | |
| WO | WO-2017078022 | A1 * | 5/2017 | B25J 3/04 |
| WO | 2019/096939 | A1 | 5/2019 | |
| WO | 2021/147265 | A1 | 7/2021 | |

OTHER PUBLICATIONS

"User interface of force-controlled arm for endoscopic surgery;" Kasai et al., 2017 IEEE/RSJ International Conference on Intelligent Robots and Systems (IROS) (2017, pp. 6477-6483); Jan. 19, 2018. (Year: 2018).*

"Development of independently-controlled position and orientation manipulator for minute work;" Tokashiki et al., Proceedings 2000 ICRA. Millennium Conference. IEEE International Conference on Robotics and Automation. Symposia Proceedings, Jan. 1, 2000. (Year: 2000).*

Sep. 28, 2021 International Search Report issued in International Patent Application No. PCT/JP2021/029865.

Feb. 13, 2024 International Preliminary Report on Patentability issued in International Patent Application No. PCT/JP2021/029865.

Sep. 16, 2024 extended Search Report issued in European Patent Application No. 21954116.6.

* cited by examiner

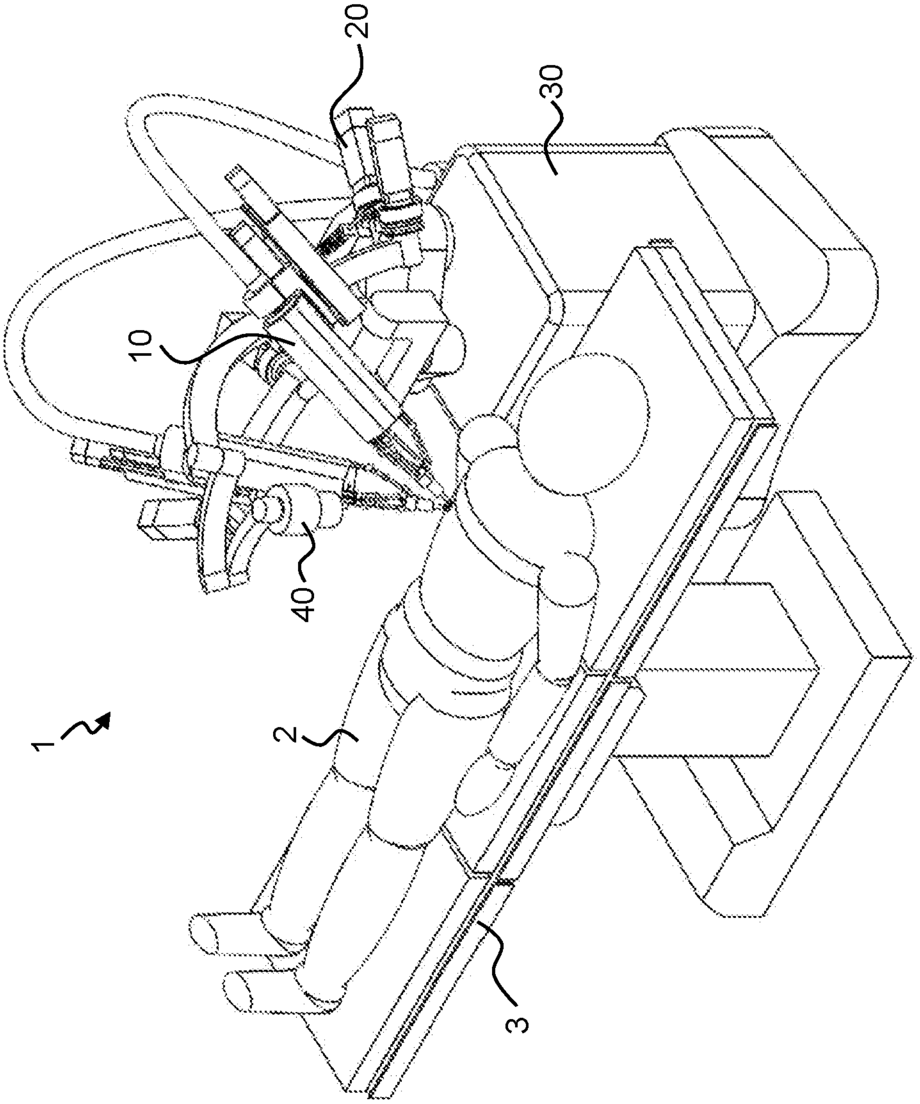
【FIG. 1】

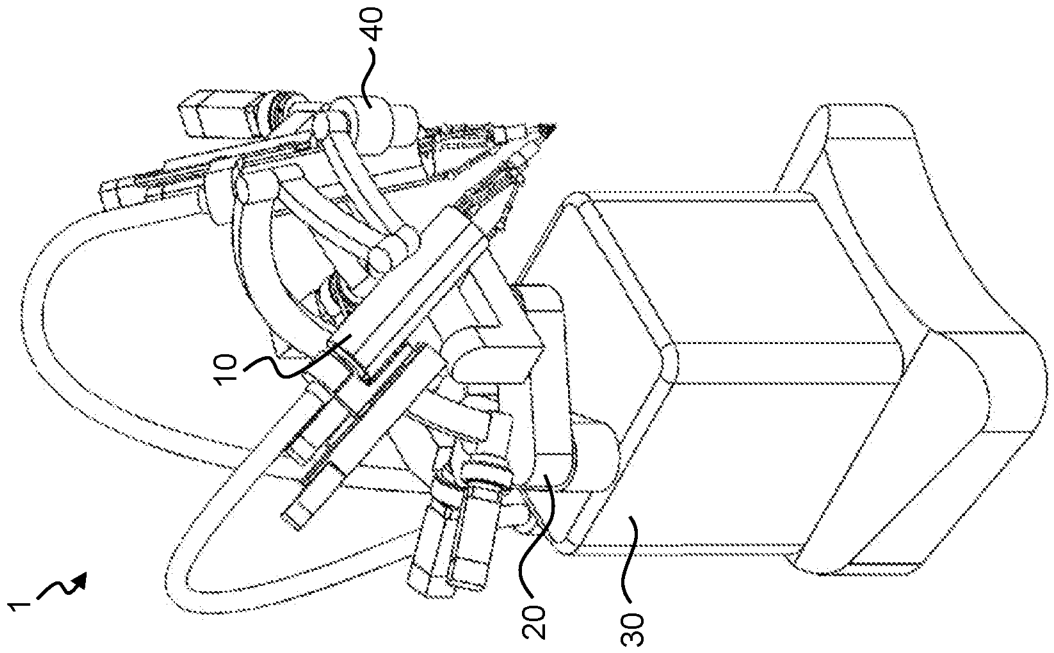
【FIG. 2】

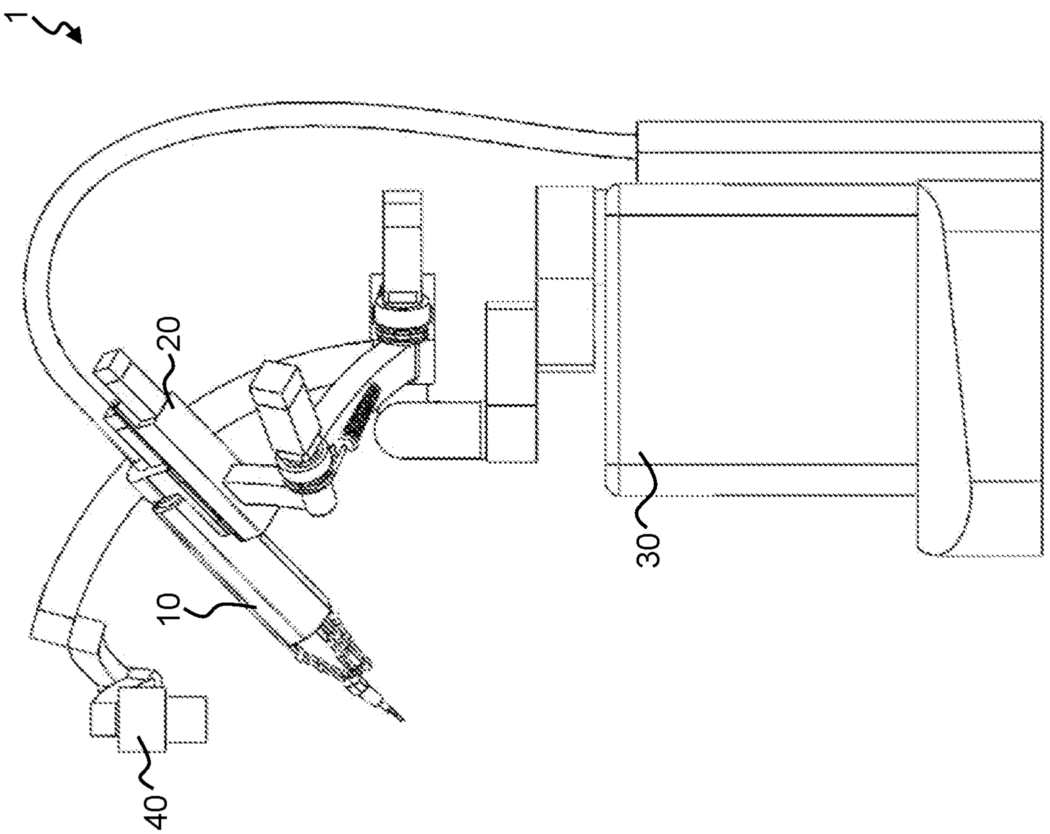
【FIG. 3】

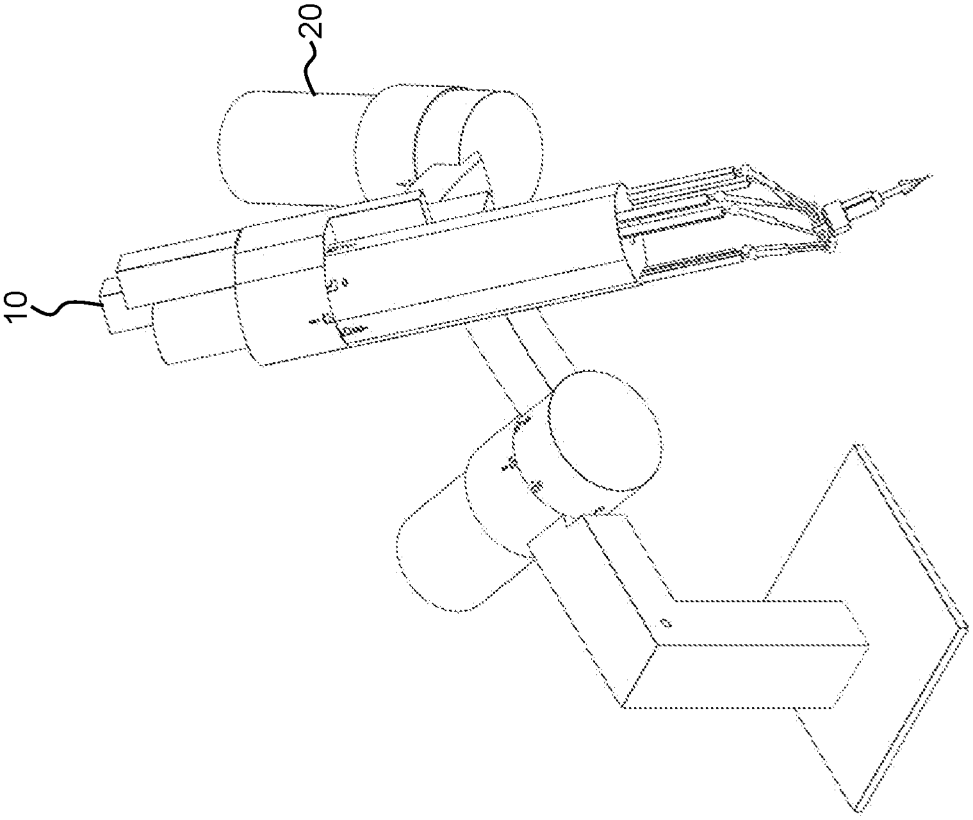
【FIG. 4】

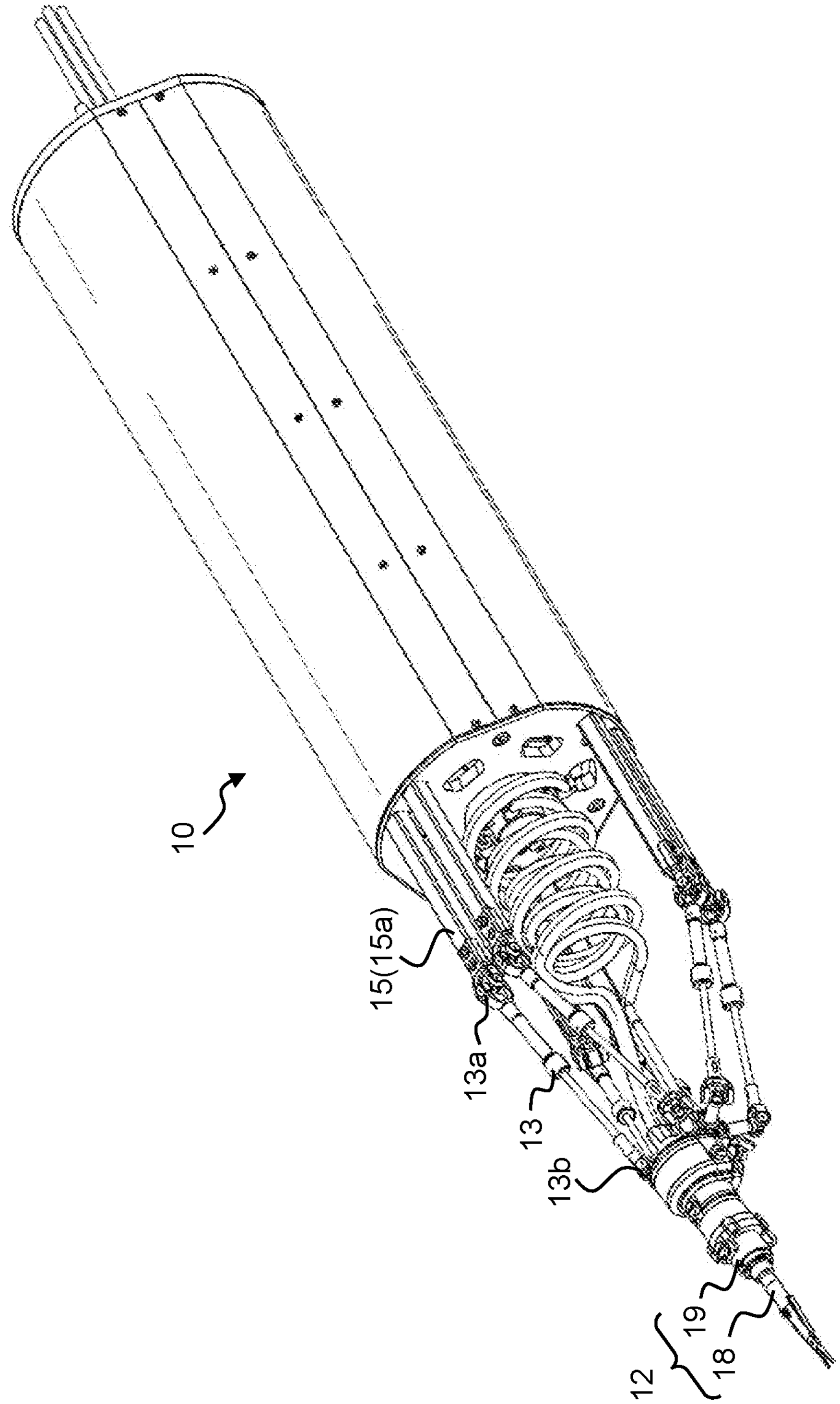
【FIG. 5】

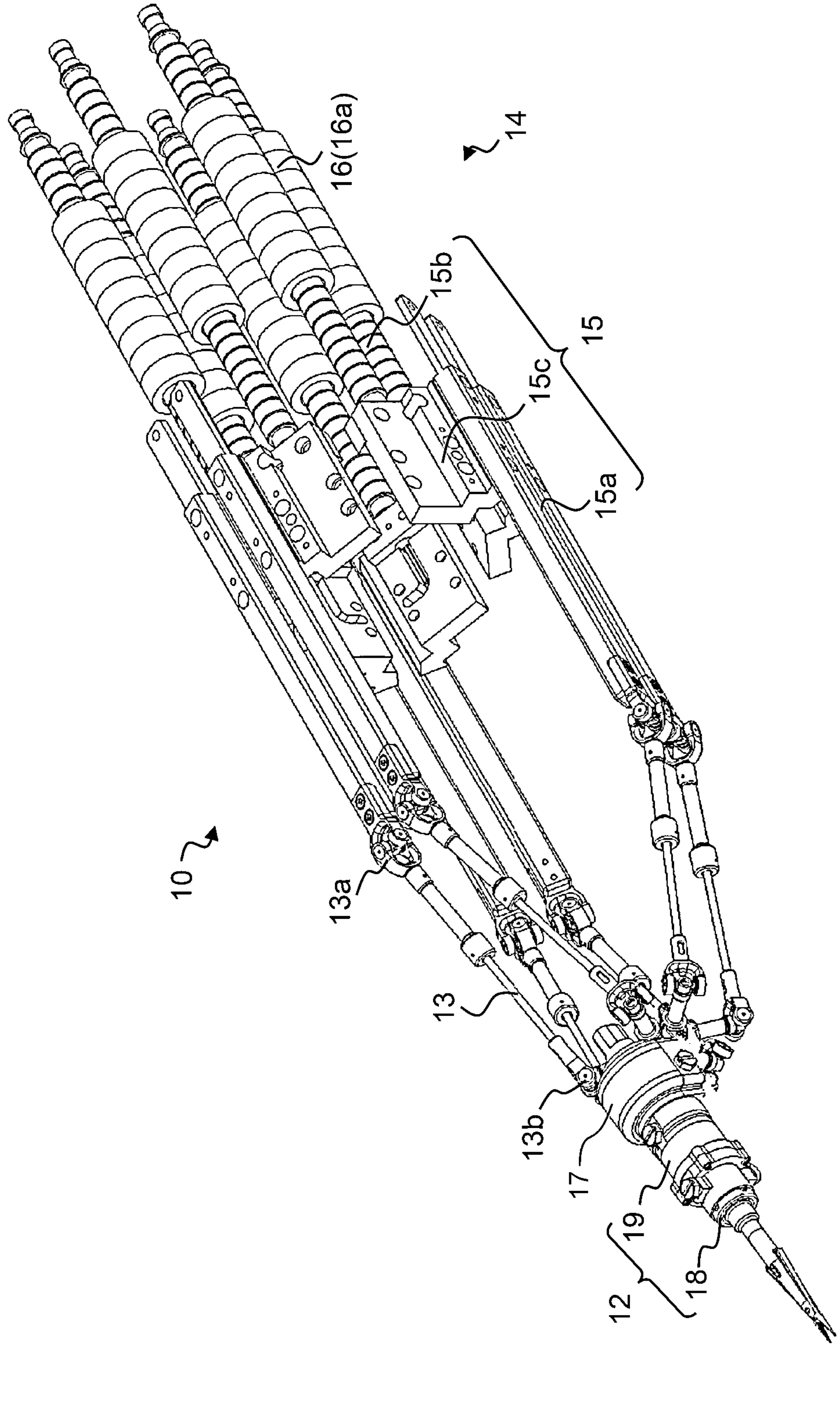
[FIG. 6]

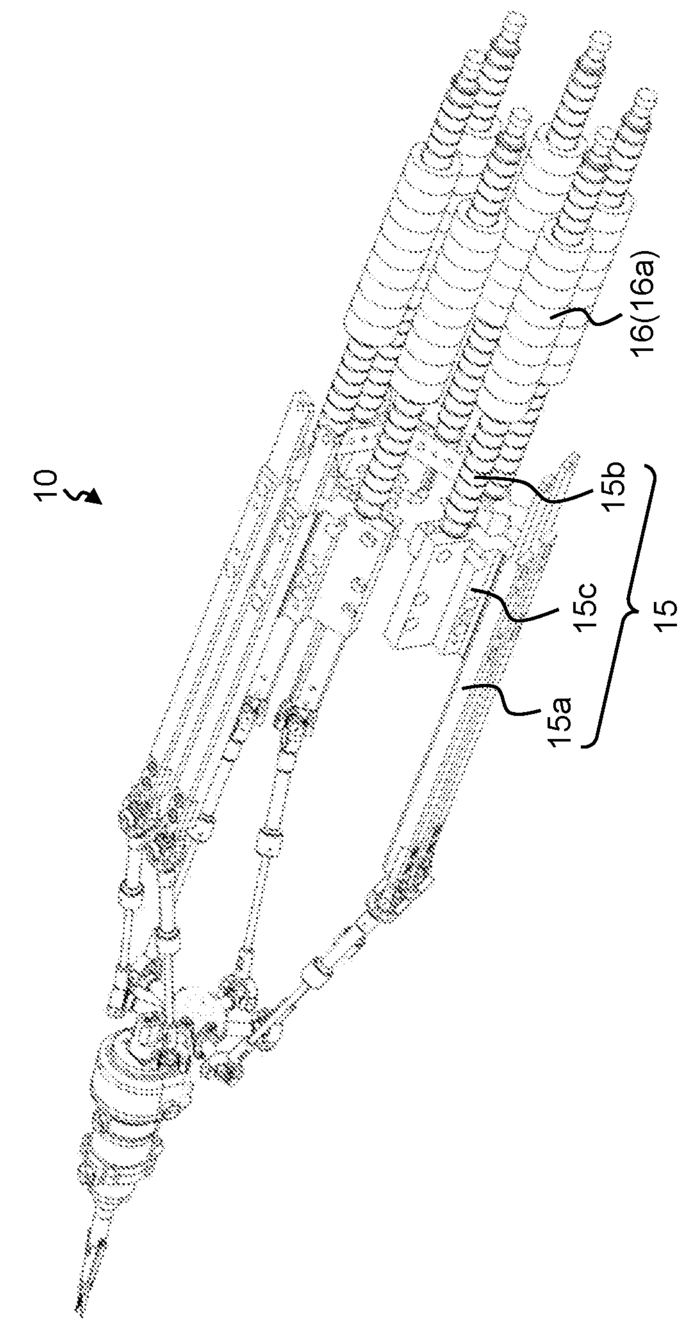
【FIG. 7】

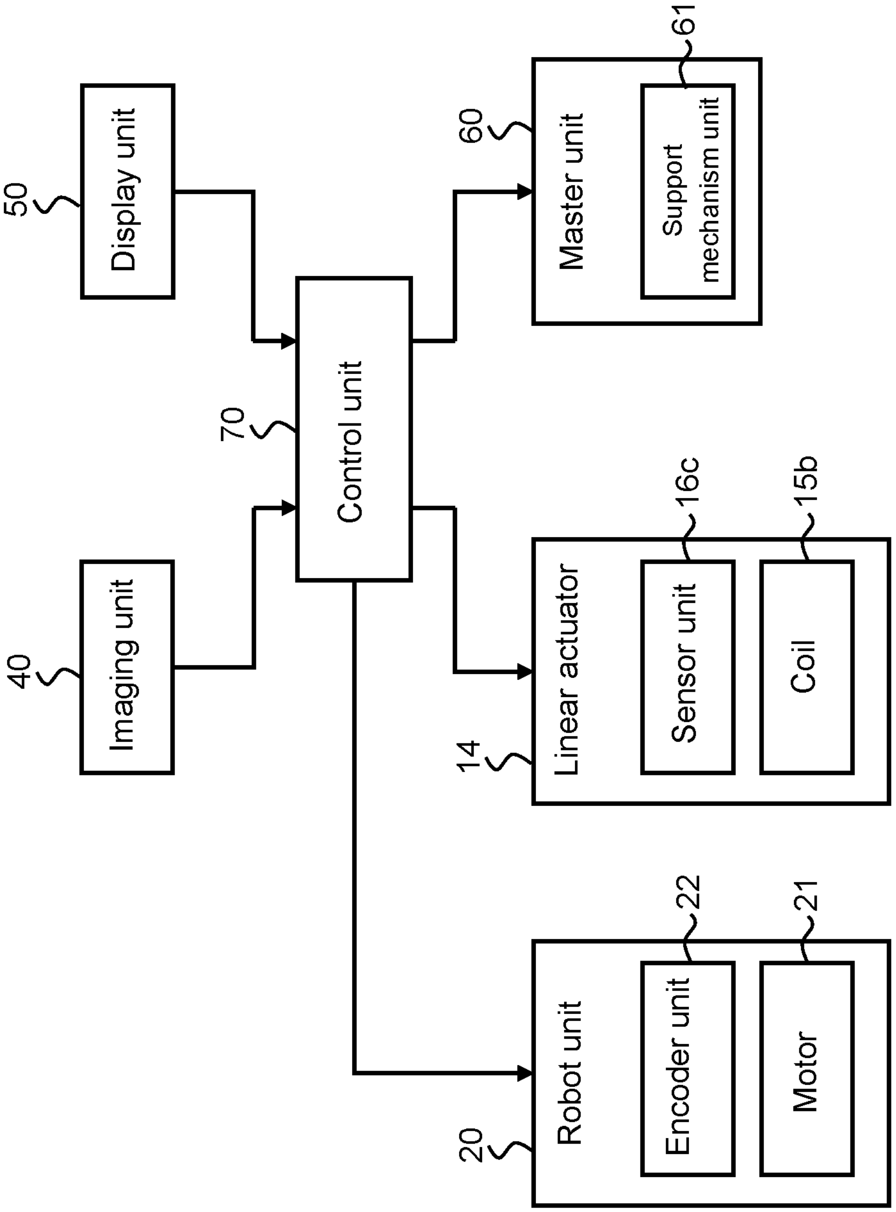
【FIG. 8】

【FIG. 9】
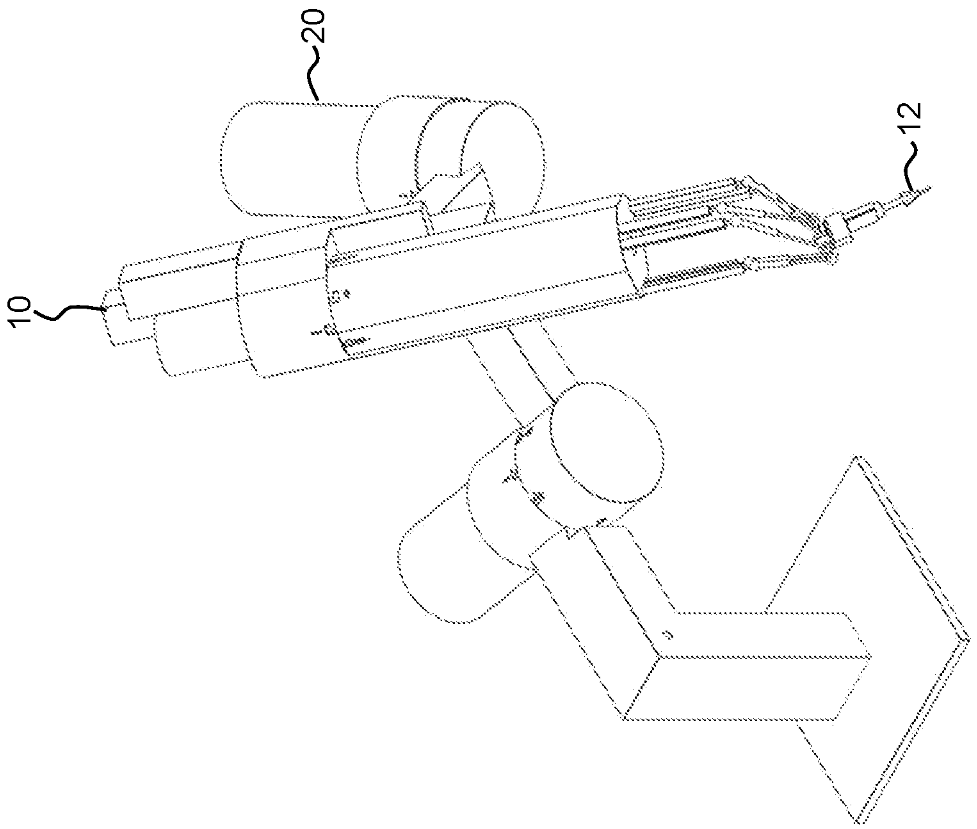

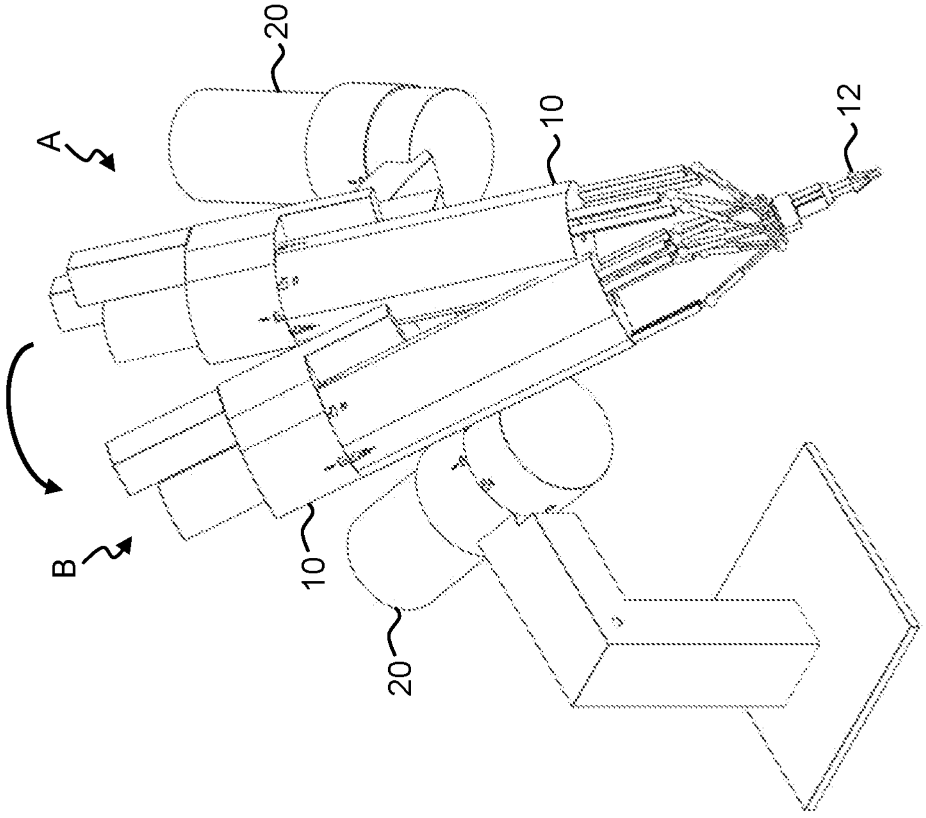
【FIG. 1 0】

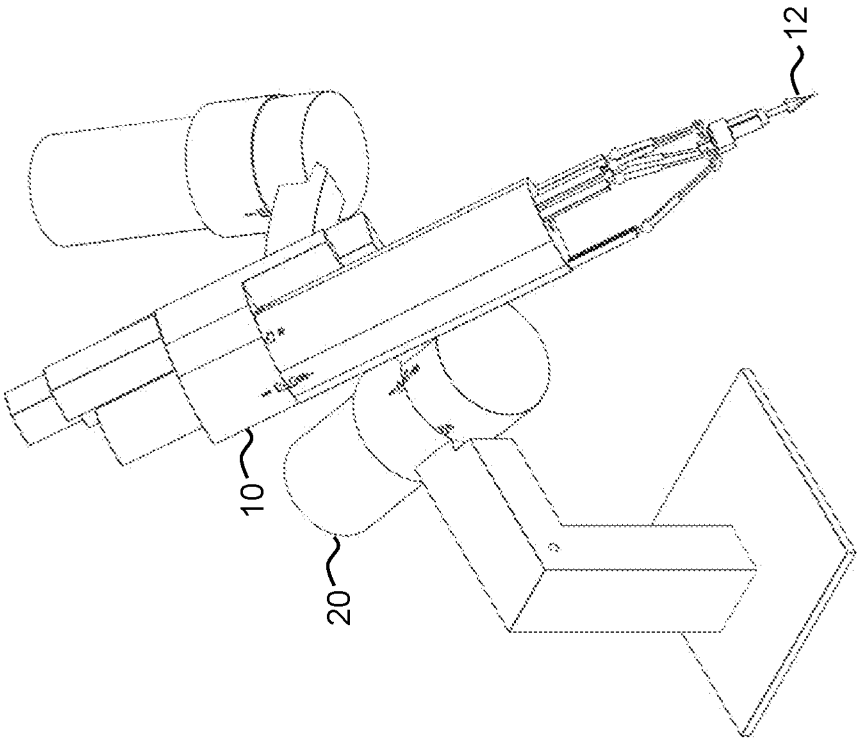
【FIG. 11】

【FIG. 1 2】
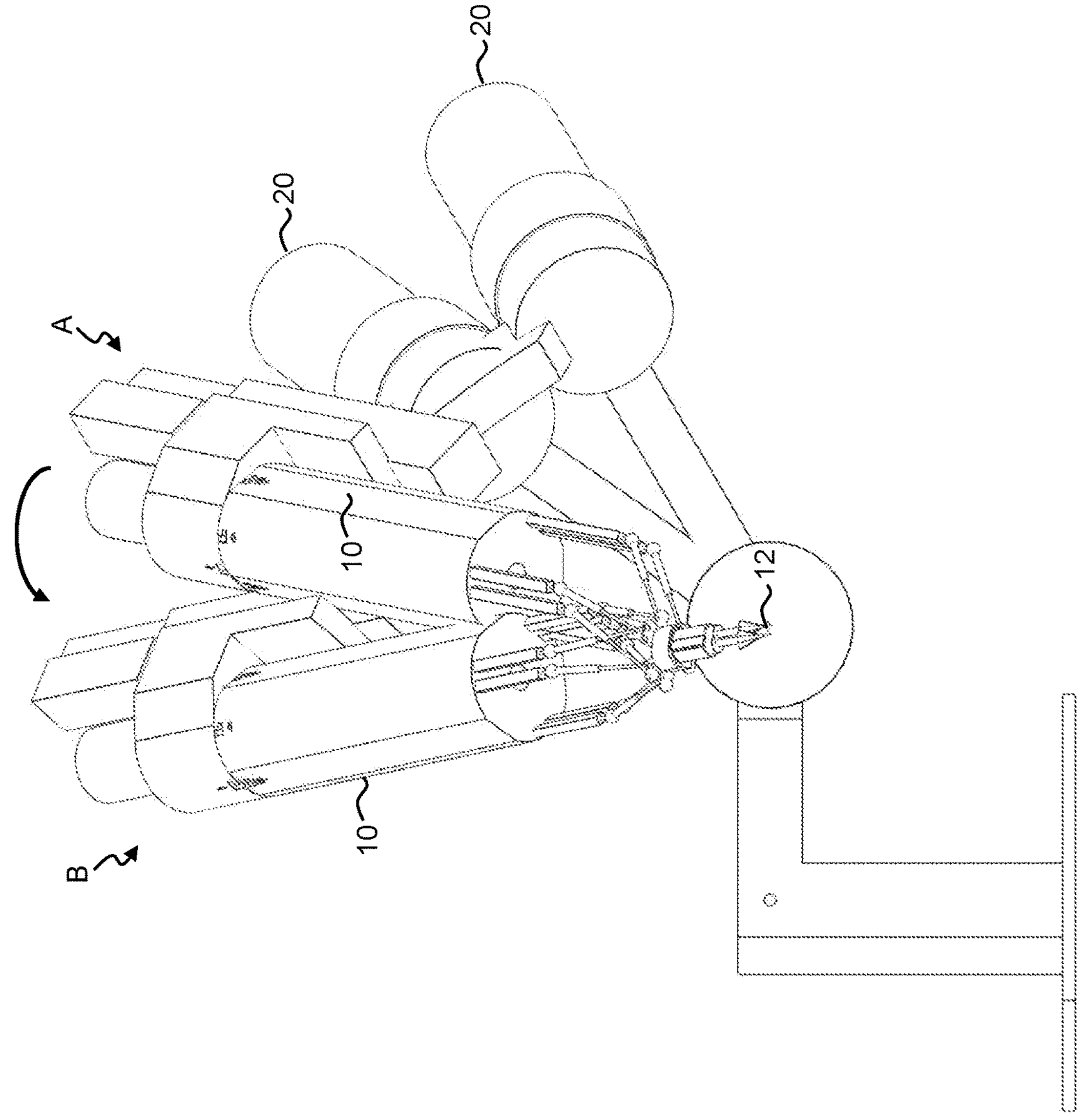

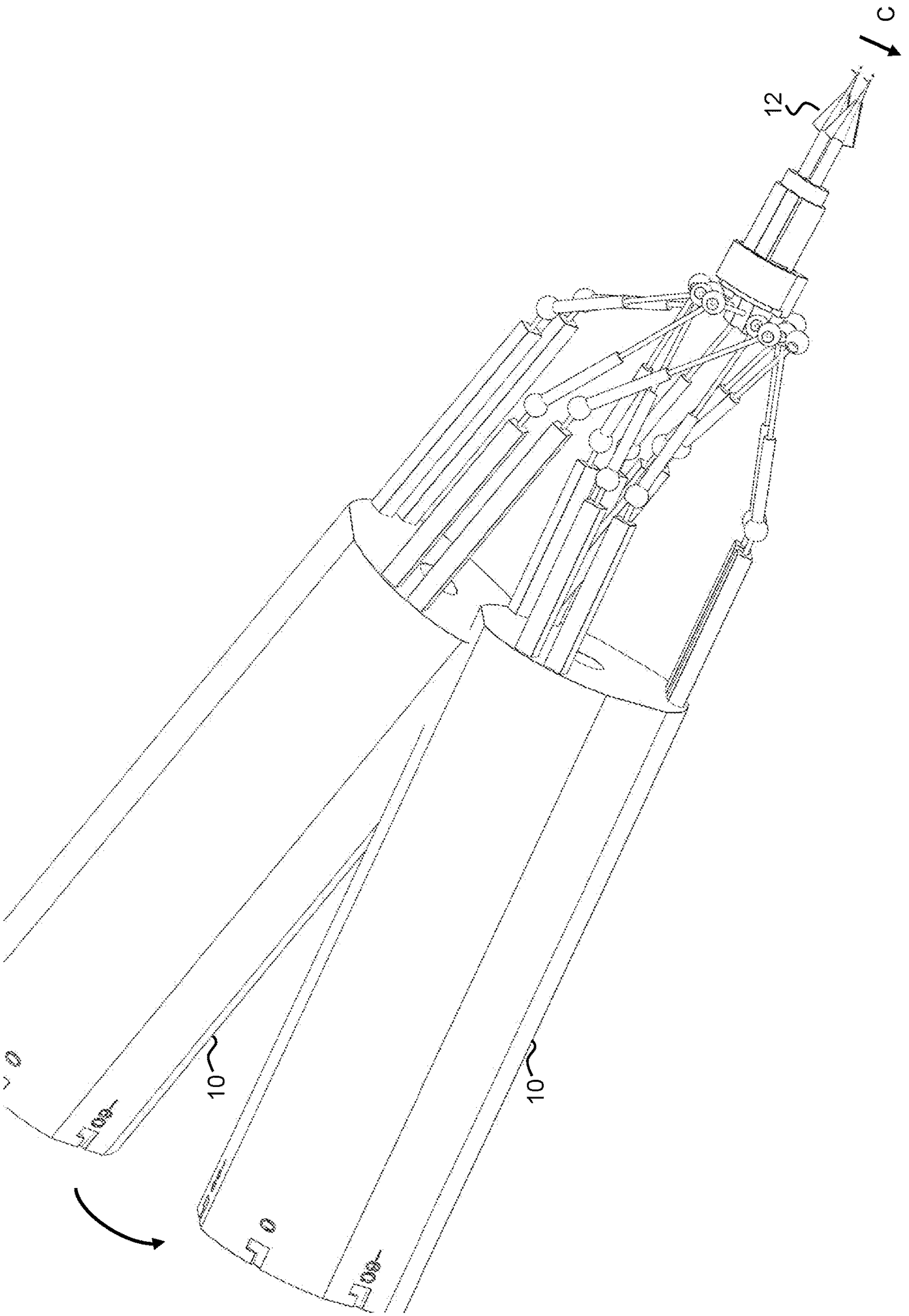
【FIG. 1 3】

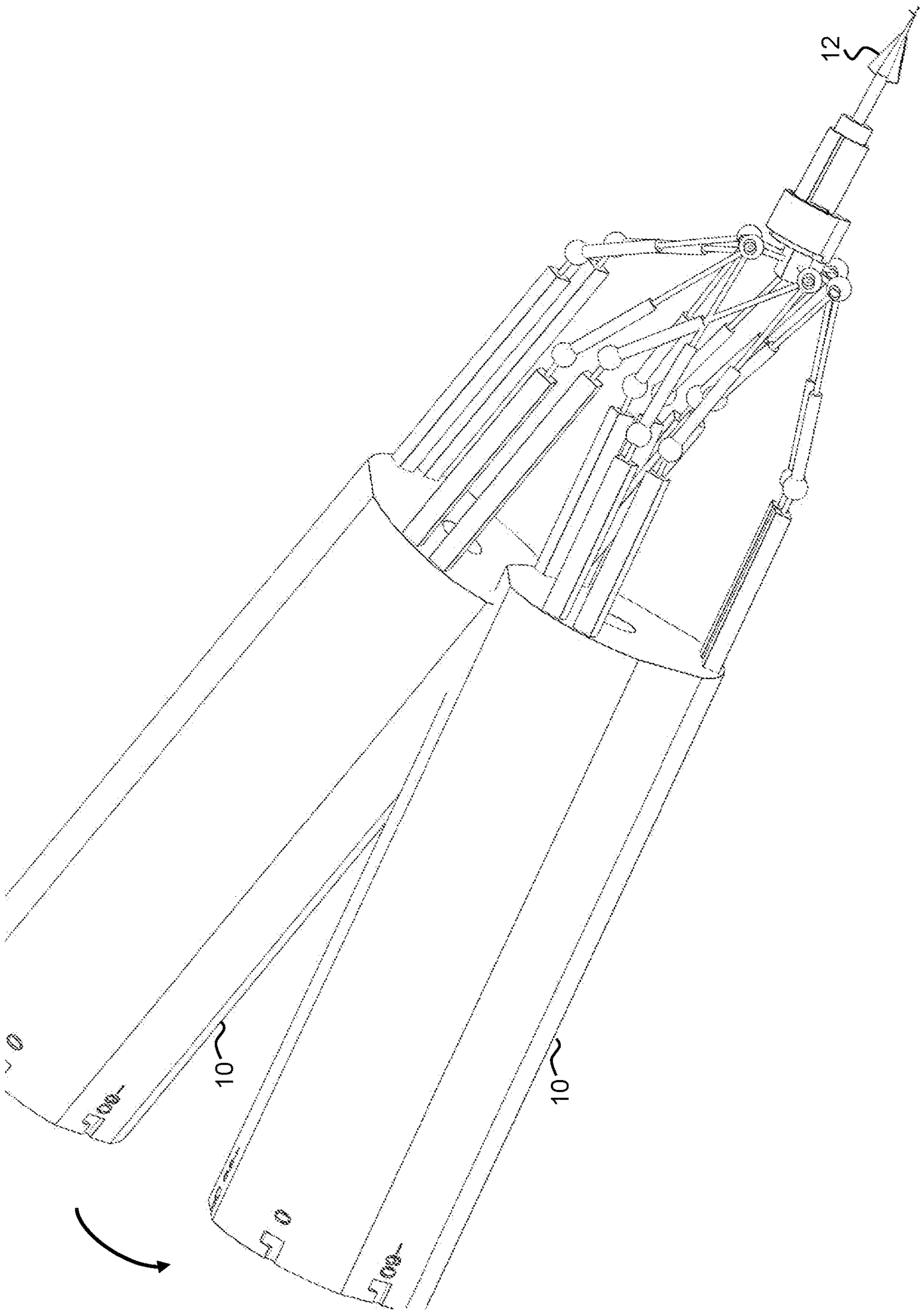
【FIG. 1 4】

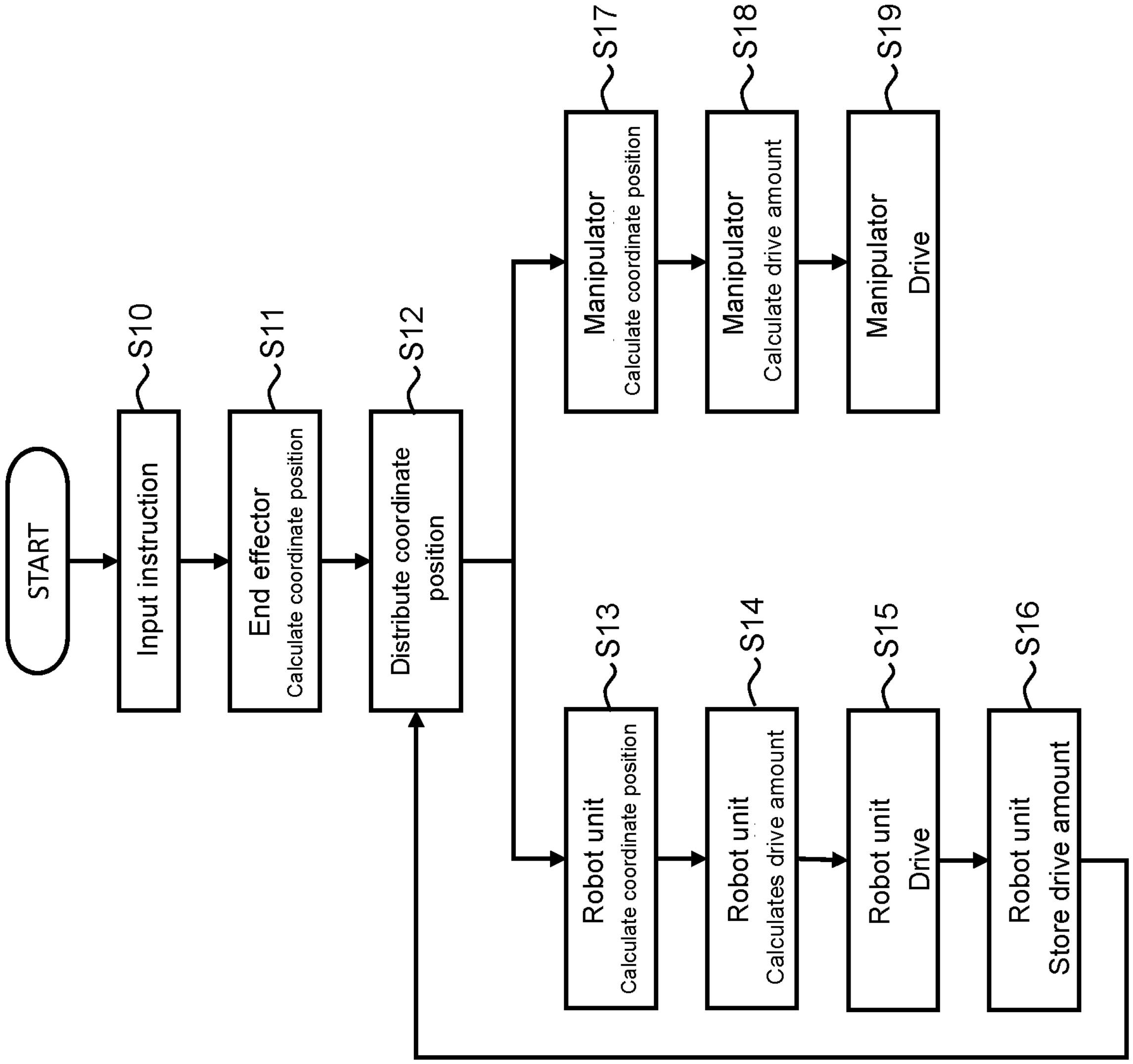
【FIG. 1 5】

DEVICE FOR FINE WORK

TECHNICAL FIELD

The present invention relates to a device for fine work.

BACKGROUND ART

In surgery relating to orthopedic surgery and plastic surgery, reconstructive surgery for lost parts, and so forth, so-called microsurgery in which surgery is performed under microscope on minute objects of surgery, such as anastomosis and so forth of fine blood vessels, nerves, and lymph ducts that are around 0.5 to 2 mm in diameter, requires extremely precise and accurate work since the objects of surgery are small, and expertise is required for the surgery. Also, the surgery tends to last for many hours due to the difficulty thereof, and in the case of such prolonged surgery, the burden on the surgeon is great. Due to such situations, with regard to microsurgery, the number of surgeons who can perform surgery is limited despite increasing demand therefor, and surgery has not been performed frequently.

Now, study on utilization of manipulators (robots) which have markedly advanced technologically in recent years, master-slave manipulators are not only capable of reproducing motions of humans true to the original, but also of performing operations in which motions of humans are scaled down. There is expectation that having manipulators that operate with precision take over operations relating to surgery could reduce the burden on the surgeon, with precision being ensured by eliminating effects of shaking of hand movements and so forth, thereby improving efficiency of surgery.

Accordingly, the present inventors have proposed a fine work assistance system that is capable of efficient work assistance by causing operations relating to work to be appropriately performed by remote operations, and of alleviating burdens on workers, and a fine work manipulator used in the same (see PTL 1).

CITATION LIST

Patent Literature

[PTL 1]
Japanese Patent Application Publication No. 2017-87322

SUMMARY OF INVENTION

Technical Problem

In the fine work manipulator disclosed in PTL 1, forceps provided on a tip portion thereof are operated by a parallel link mechanism. Now, the parallel link mechanism has a certain operable range, and beyond this operable range, the forceps on the tip portion cannot be moved as intended, and eventually come to a stop. Before this occurs, if a robot unit supporting the parallel link mechanism is rotated and the parallel link mechanism is moved so as to near an initial position, then an operating range for the forceps on the tip portion is ensured and fine work can be consecutively performed without stopping.

The parallel link portion has six degrees of freedom in the technology disclosed in PTL 1, but the robot unit has a configuration with four degrees of freedom since it is intended to reduce the size of the robot unit. Contents of the four degrees of freedom is three degrees of freedom in rotational directions+one degree of freedom for radial direction translation in a coordinates system, and there is no movement of translation in the two directions perpendicular to the radius that are necessary for six degrees of freedom.

Accordingly, even if the robot unit is moved so that the parallel link mechanism is at the initial position, the movement in the two directions of translation cannot be performed, resulting in a displacement of the tip of the forceps.

However, in the present device for fine work, fine work is performed, and accordingly displacement in the two directions of translation is no greater than around ±15 mm at the most, which is not very great.

When a forceps portion at the tip portion moves due to the robot unit moving, fine work is affected, but by correcting this movement, which is not very great, in the two directions of translation through operations of the parallel link mechanism, the forceps at the tip portion no longer moves after this correction. Also, the parallel link mechanism is in a state that is almost the same as the initial position, and the operating range of the forceps at the tip portion is ensured.

The present invention has been made in light of the above problem, and it is an object thereof to provide a device for fine work that is capable of securing an operating range for fine work without causing change in a position of performing fine work.

Solution to Problem

In order to solve the above problem, a device for fine work according to an aspect of the present invention is a fine work device executing a predetermined operation relating to fine work with respect to an object of work, in place of a person. The fine work device has a fine work manipulator that is configured to perform the fine work and that has a predetermined operating range, a robot unit that is configured to support the fine work manipulator and that has a wider operating range than the operating range, and a control device that is configured to control driving of the fine work manipulator and the robot unit. The control device accepts input of movement of a tip position of the fine work manipulator, which is an operating position of the fine work, and, with the operating position being a target position, calculates drive amounts of the fine work manipulator and the robot unit, and controls operation of the fine work manipulator and the robot unit on the basis of the drive amounts.

Advantageous Effects of Invention

According to the present invention, a fine work device can be realized that is capable of ensuring an operating range for fine work, without causing variation in a position for performing the fine work.

BRIEF DESCRIPTION OF DRAWINGS

FIG. 1 is a perspective view illustrating a schematic configuration of a fine work device according to an embodiment.

FIG. 2 is a perspective view illustrating a schematic configuration of the fine work device according to the embodiment.

FIG. 3 is a side view illustrating a schematic configuration of the fine work device according to the embodiment.

FIG. 4 is a perspective view illustrating a schematic configuration of a fine work manipulator and a robot unit of the fine work device according to the embodiment.

FIG. 5 is a perspective view illustrating the fine work manipulator of the fine work device according to the embodiment.

FIG. 6 is a perspective view illustrating principal portions of the fine work manipulator of the fine work device according to the embodiment.

FIG. 7 is a perspective view illustrating principal portions of the fine work manipulator of the fine work device according to the embodiment.

FIG. 8 is a block diagram illustrating a schematic configuration of the fine work device according to the embodiment.

FIG. 9 is a perspective view illustrating an example of operations of the fine work device according to the embodiment.

FIG. 10 is a perspective view illustrating another example of operations of the fine work device according to the embodiment.

FIG. 11 is a perspective view illustrating yet another example of operations of the fine work device according to the embodiment.

FIG. 12 is a side view illustrating an example of operations of the fine work device according to the embodiment.

FIG. 13 is a perspective view illustrating an example of operations of the fine work manipulator of the fine work device according to the embodiment.

FIG. 14 is a perspective view illustrating another example of operations of the fine work manipulator of the fine work device according to the embodiment.

FIG. 15 is a flowchart showing an example of operations of the fine work device according to the embodiment.

DESCRIPTION OF EMBODIMENTS

An embodiment of the present invention will be described below with reference to the drawings. It should be noted that the embodiment described below does not limit the invention according to the claims, and that not all elements and combinations thereof described in the embodiment are necessarily essential to the solving means of the invention.

Note that in the drawings by which the embodiment is described, parts that have the same function are denoted by the same sign, and repetitive description thereof will be omitted.

In the present embodiment, description will be made regarding a fine work device, to which is applied a fine work manipulator for surgery assistance that handles microsurgery which is fine work.

As illustrated in FIG. 1 to FIG. 4 and FIG. 8, the fine work device 1 according to the present embodiment includes a fine work manipulator 10, a robot unit 20, on a tip portion of which is attached this fine work manipulator 10, a base 30 that supports this robot unit 20 from below, an imaging unit 40 that is similarly attached to the base 30 and that performs imaging of objects of surgery, a display unit 50 that enlarges images of the object of surgery acquired by the imaging unit 40 and performs display thereof so as to be viewable by a user, a master unit 60 that receives input instructions from the user, and a control unit 70 that performs control of moving the fine work manipulator 10 and the robot unit 20 in accordance with the master unit 60 that is moved by the user.

The master unit 60 includes an operation input unit, omitted from illustration, which receives operations by the user, and a support mechanism unit 61 that is capable of acquiring information regarding position and orientation of the operation input unit while movably supporting this operation input unit.

The robot unit 20 has three rotational degrees of freedom and one translation degree of freedom in the radial direction. The robot unit 20 has a motor 21, and an encoder unit 22 (omitted from illustration in FIG. 1 to FIG. 4, see FIG. 8) that detects a rotational angle of the motor 21. Although a pair of the robot unit 20 and the fine work manipulator 10 is provided on the base 30 in the illustrated example, the number of the robot units 20 and the fine work manipulators 10 is not limited in particular.

The imaging unit 40 is for performing imaging of a tip operating portion of an end effector of the fine work manipulator 10 that will be described later, and the object of surgery, and is disposed at a position enabling a plane view of at least a tip portion of the fine work manipulator 10 and the object of surgery, above the robot unit 20 or the like, for example. This imaging unit 40 is a known video camera that is capable of acquiring high-resolution imaged images, in which reproducibility can be ensured even when enlarging to the same scale as viewing with a conventional microscope for microsurgery, and accordingly detailed description will be omitted here.

The display unit 50 is for enlarging the image of the object of surgery acquired by the imaging unit 40 as necessary, and performing display thereof so as to be viewable by the user. This display unit is a known display device such as a liquid crystal display or the like that is capable of high-resolution display of the images acquired by imaging, and accordingly detailed description will be omitted here.

The base 30 has a moving mechanism that is omitted from illustration, and is configured to be capable of moving over a floor of an operating room that is omitted from illustration, along with the fine work manipulator 10, the robot unit 20, and the imaging unit 40 that are provided on this base 30, to a predetermined position on the basis of moving support from the control unit 70. Accordingly, the fine work device 1 according to the present example is capable of coming closer to and away from a surgery table 3 on which a patient 2 that is the object of surgery illustrated in FIG. 1 lies, and further, at least the tip portion of the fine work manipulator 10 can be disposed at a surgery position of the patient 2.

Next, the fine work manipulator 10 will be described with reference to FIG. 5 to FIG. 7.

The fine work manipulator 10 has a base, omitted from illustration, which is supported by the robot unit 20, an end effector 12 that handles the object of surgery or surgical equipment, six links 13 that are disposed in parallel, and six linear actuators 14 that are supported by the base and that move the links 13.

The base, the end effector 12, the links 13, and the linear actuators 14 make up a parallel link mechanism with six degrees of freedom that, at each link 13, causes linear motion of one end portion of the link 13 by the linear actuator 14, thereby moving the end effector 12 linked to the ether end of the link 13.

The parallel link mechanism makes position and orientation of the end effector 12 that handles the object of surgery or the surgical equipment to be variable as to the base, within a predetermined range, and by having six degrees of freedom, the end effector 12 on a tip thereof is given movement equivalent to that in a case of being supported by a hand.

The linear actuators 14 are moving coil linear motors in which coils 15*b* are part of moving elements 15, and permanent magnets 16*a* are part of stationary elements 16. Sensor units 16*c* (omitted from illustration in FIG. 5 to FIG.

7, see FIG. 8) that detect amount of movement of the moving elements 15 are provided to the stationary elements 16.

The moving elements 15 have linear-motion sliders 15*a* that are disposed so as to be capable of linear movement with respect to the base, slender cylindrically-disposed coils 15*b* that are integrally attached in an orientation in which a direction of movement is parallel to these linear-motion sliders 15*a*, and linking members 15*c* that are attached to tips of the coils 15*b* and that link these coils 15*b* and the linear-motion sliders 15*a*. One end portions of the links 13 are fixed by linking to tips of the linear-motion sliders 15*a* of the moving elements 15, and the one end portions of these links 13 linearly move with the moving elements 15 including the linear-motion sliders 15*a*.

The stationary elements 16 are formed in cylinder shapes that are greater in diameter and shorter than the coils 15*b* of the moving elements 15, and have the permanent magnets 16*a* that are fixed to the base by fixing means omitted from illustration.

In the stationary elements 16, the cylindrical permanent magnets 16*a* that are fixed to the base are disposed in a state in which a cylindrical axial direction matches that of the coils 15*b* of the moving elements 15, and the coils 15*b* movably pass through space portions inside the cylinders of the permanent magnets 16*a*.

Due to using the linear actuators 14 as linear motors in this way, mechanical moving parts can be reduced as compared to other linear motion mechanisms such as ball joints and so forth, and moreover, contact portions that involve sliding and turning can be reduced, backlash does not occur, reliability of the mechanism is improved, and furthermore, electric power consumption needed for driving can be suppressed due to reduced frictional resistance.

The linear actuators 14 that are linear motors made up of the moving elements 15 and the stationary elements 16 are in a state of being disposed arrayed with the movement directions of each of the moving elements 15 being in parallel with each other, and, about a predetermined imaginary center line that is parallel to the movement directions of the moving elements 15 and extends in a longitudinal direction of the linear actuators 14, the permanent magnets 16*a* of the stationary elements 16 and the coils 15*b* of the moving elements 15 are on the closest side to the imaginary center line, and the permanent magnets 16*a* and the coils 15*b* are each disposed equidistantly about the imaginary center line.

Note that one permanent magnet 16*a* making up one stationary element 16 is also disposed close to other coils 15*b* besides the coil 15*b* that passes through the cylindrical space portion thereof and makes up a linear motor set, but there is no variation in magnetic field of the permanent magnets 16*a* that are fixed, unlike the coils 15*b*, and accordingly does not magnetically affect movement of the other coils 15*b*.

The moving elements 15 and the stationary elements 16 making up the linear actuators 14 are disposed arrayed about the virtual center line, and accordingly the linear actuator portions of the fine work manipulator 10 can be packed into a compact structure. Further, the end portions of the coils 15*b* of the moving elements 15 at which the magnetic fields are made to vary do not come very close to the permanent magnets 16*a* of the stationary elements 16 with respect to the mechanical structure, and accordingly variation in magnetic fields that causes cogging with regard to movement of the moving elements 15 can be suppressed, and smooth operations of the linear actuators 14 can be realized.

The links 13 have configurations in which joints 13*a* and 13*b*, having a plurality of degrees of freedom for linking to each of the linear actuators 14 and a turning support portion 17, are disposed at the respective ends of rod-like members in which two substantially rod-like members that are highly rigid and do not deform are combined by being linked in the longitudinal direction. In these links 13, the substantially rod-like members making up the rod-like members are linked so as to be rotatable as to each other, and are structures that impart a rotational degree of freedom as to each other about an axis parallel to the longitudinal direction, between a portion toward one end of the links 13 and a portion toward the other end thereof.

The joints 13*a* on the one end portions of the links 13 each have structures having a rotational degree of freedom about two axes that are orthogonal to each other, and are linked to the end portions of the linear-motion sliders 15*a* of the linear actuators 14. Also, the joints 13*b* on the other end portions of the links 13 each have structures having a rotational degree of freedom about two axes that are orthogonal to each other, similar to the above, and are linked to the turning support portion 17.

By imparting the rotational degree of freedom between the portions of the links 13 toward one end and the portions toward the other end, and linking by the joints 13*a* and 13*b* that have two rotational degrees of freedom at respective end portions of the links 13, the links 13 can freely change their orientation with respect to the linear actuators 14 and the turning support portion 17 to which they are linked, in the same way as a case of linking using ball joints. Also, by forming the link mechanism in which such links 13 are disposed between the linear actuators 14 and the turning support portion 17 as a parallel link mechanism in which six links 13 are arrayed in parallel, an arrangement is made in which various types of movements regarding change in the position and orientation of the turning support portion 17 and the end effector 12 provided on a tip portion of the turning support portion 17 can be permitted with respect to the base, in six degrees of freedom obtained by combining the three degrees of freedom of movement in three axial directions orthogonal to each other, and each of the three degrees of freedom of rotation about the three axes, in the same way as in a case of supporting the end effector 12 by a human hand.

Next, operations of the fine work device 1 according to the present embodiment, in particular the operations of the robot unit 20 and the fine work manipulator 10, will be described with reference to FIG. 9 to FIG. 14.

As described above, the parallel link mechanism of the fine work manipulator 10 has the six degrees of freedom. Accordingly, when performing fine work by the end effector 12 after moving the base 30 to a predetermined position and fixing the three-dimensional position and the rotational position of the fine work manipulator 10 at a predetermined position by the robot unit 20, the fine work can be performed only primarily by the operations of the parallel link mechanism that has the six degrees of freedom. However, there is a certain limit to the operable range of the parallel link mechanism, and in a case of moving the tip of the end effector 12 beyond this operable range, there is a need to change the position of the fine work manipulator 10 itself by the robot unit 20 while returning the parallel link mechanism to the initial position, i.e., to a position of being symmetrical with respect to the center axis of the fine work manipulator 10.

FIG. 9 is a diagram illustrating the fine work manipulator 10 in which the parallel link mechanism is near the operable range. In the Figure, the end effector 12 is near the operable range of the parallel link mechanism in a lower left direction in the Figure, and in order to move the end effector 12 further in the lower left direction in the Figure, there is a need to operate the robot unit 20 while returning the parallel link mechanism to the initial position, and compensate for movement of a tip position of the end effector 12 due to returning the parallel link mechanism to the initial position.

In the example illustrated in FIG. 10, the parallel link mechanism is returned to the initial position while causing the fine work manipulator 10 to rotationally move (position to which rotational movement was made is indicated by B in the Figure) by turning to the left direction in the Figure (counterclockwise direction) from a position of the fine work manipulator 10 illustrated in FIG. 9 (indicated by A in the Figure), by operation of the robot unit 20. Accordingly, the operating range of the parallel link mechanism is ensured again, as illustrated in FIG. 11.

However, in the fine work device 1 according to the present embodiment, the robot unit 20 only has three rotational degrees of freedom and one degree of freedom for radial direction translation, and accordingly, simply performing rotational movement of the fine work manipulator 10 by the robot unit 20 while returning the parallel link mechanism to the initial position may cause parallel movement of the position of the end effector 12 (parallel movement in the Figures indicated by C), as illustrated in FIG. 12 and FIG. 13.

Accordingly, in the fine work device 1 according to the present embodiment, the fine work manipulator 10 and the robot unit 20 are synchronized such that there is no parallel movement of the position of the end effector 12. In the example illustrated in FIG. 14, rotational movement of the fine work manipulator 10 is performed by the robot unit 20 while returning the parallel link mechanism close to the initial position such that the tip position of the end effector 12 does not move, i.e., with the tip position of the end effector 12 as a control target position.

Accordingly, the fine work device 1 can be realized in which the operating range for fine work by the fine work manipulator 10 can be ensured, while maximally suppressing variation in the position of the end effector 12 that performs fine work.

FIG. 15 is a flowchart showing an example of operations of the fine work device 1 according to the present embodiment.

First, the user performs operation input instruction for the fine work device 1 by operating the master unit 60, and the control unit 70 accepts this operation input instruction (step S10).

Next, the control unit 70 calculates a coordinate position and a rotational angle to serve as a target for the tip of the end effector 12, on the basis of the operation input instruction (step S11). The control unit 70 then decides a distribution of operations between the robot unit 20 and the fine work manipulator 10, on the basis of the coordinate position of the tip of the end effector 12 calculated in step S11 (step S12).

In the work in step S12, the control unit 70 distributes operations between the robot unit 20 and the fine work manipulator 10, so as to position the end effector 12 at the coordinate position and the rotational angle serving as the target for the tip of the end effector 12. The technique for distributing is optional, and may be realized just by operations of the fine work manipulator 10 (i.e., operations of the parallel link mechanism), for example, may be realized by collaborative work between the fine work manipulator 10 and the robot unit 20, or may be performed by operations of the robot unit 20 alone.

Detailed operations of step S12 will be described by way of an example. In order to position the end effector 12 at the coordinate position and the rotational angle serving as the target for the tip of the end effector 12, first, the control unit 70 distributes the operations between the robot unit 20 and the fine work manipulator 10 under conditions of moving only the parallel link mechanism of the fine work manipulator 10. Determination is then made regarding whether or not the coordinate position and the rotational angle of the fine work manipulator 10 that is distributed has neared a certain threshold value with respect to an operation limit of the parallel link mechanism of the fine work manipulator 10. Examples of the threshold values include that the joints 13*a* and 13*b* making up the parallel link mechanism are 5 degrees short of interfering with each other, that intervals between adjacent links 13 of the parallel link mechanism are within 3 mm, and so forth.

When judging that the threshold value is being neared, the control unit 70 then decides the coordinate position and the rotational angle of the parallel link mechanism of the fine work manipulator 10 so as to return the parallel link mechanism of the fine work manipulator 10 to the initial position, and meanwhile, decides the coordinate position and the rotational angle of the robot unit 20 so as to position the end effector 12 at the coordinate position and the rotational angle serving as the target for the tip of the end effector 12 by operating the robot unit 20.

At this time, setting an operating speed of the robot unit 20 to 100% of output of the motor making up this robot unit 20 may cause the tip portion of the end effector 12 to vibrate. Conversely, making the operating speed of the robot unit 20 to be too slow may cause the parallel link mechanism of the fine work manipulator 10 to reach an operation limit at an early stage, since operations by the master unit 60 are continuing. Accordingly, setting the operating speed of the robot unit 20 to be variable within a range of 10% to 60%, as one example, so as to be settable by an operator in accordance with contents of operation by the fine work manipulator 10, is preferable.

Thereafter, the control unit 70 calculates the coordinate position and the rotational angle of the robot unit 20 (step S13), calculates a drive amount of the motor 21 of the robot unit 20 (step S14), drives the motor 21 of the robot unit 20 on the basis of the drive amount that is calculated (step S15), and stores the drive amount of the robot unit 20 on the basis of an output value from the encoder unit 22 (step S16). Thereafter, in the distribution of operations between the robot unit 20 and the fine work manipulator 10 in step S12, the control unit 70 performs feedback control that is based on the drive amount of the robot unit 20 stored in step S16.

Meanwhile, the control unit 70 calculates the coordinate position and the rotational angle of the fine work manipulator 10 (step S17), calculates drive amounts of the linear actuators 14 of the fine work manipulator 10 (step S18), and drives the linear actuators 14 of the fine work manipulator 10 on the basis of the drive amounts that are calculated (step S19).

Note that the above embodiment is a detailed description of a configuration for explaining the present invention in an easily-understandable manner, and is not necessarily limited to an arrangement that is provided with all of the configurations described. Also, part of the configurations in the embodiments may be added to other configurations, deleted, or substituted.

As one example, the fine work manipulator 10 is attached to the robot unit 20 and the base 30 in the above-described embodiment, but a configuration may be made in which, in a state of the fine work manipulator 10 being first attached to and supported by a stand, an arm, or the like, for support thereof, coarse adjustment of the position and so forth of the fine work manipulator 10 with respect to the object of surgery is performed by a human manually moving the stand, the arm, or the like, to perform adjustment, such that the end effector 12 faces the object of surgery, and also is situated across an appropriate spacing as to the object of surgery.

Also, in the above-described embodiment, distribution of operations of the fine work manipulator 10 and the robot unit 20 is performed, but an arrangement may be made in which, for example, a foot switch for returning the fine work manipulator 10 to the initial position is provided on the master unit 60, and operation of the foot switch returns the fine work manipulator 10 to the initial position, and also sets the coordinate position and the rotational angle of the robot unit 20 such that the tip position of the end effector 12 is positioned at the position instructed by the master unit 60.

In the above-described embodiment, control lines and information lines that are thought to be necessary for description are illustrated, and all control lines and information lines of the product are not necessarily illustrated. All configurations may be mutually connected.

REFERENCE SIGNS LIST

1 Fine work device
10 Fine work manipulator
12 End effector
13 Link
14 Linear actuator
15 Moving element
15*a* Linear-motion slider
15*b* Coil
16 Stationary element
16*a* Permanent magnet
20 Robot unit
70 Control unit

The invention claimed is:

1. A device for fine work executing a predetermined operation relating to fine work with respect to an object of work, in place of a person, wherein the device for fine work has a fine work manipulator that is configured to perform the fine work and that has a predetermined operating range, a robot unit that is configured to support the fine work manipulator and that has a wider operating range than the operating range of the fine work manipulator, and a control device that is configured to control driving of the fine work manipulator and the robot unit, and the control device accepts input of movement of a tip position of the fine work manipulator, which is an operating position of the fine work, and, with the operating position being a target position, calculates drive amounts of the fine work manipulator and the robot unit, and controls operation of the fine work manipulator and the robot unit on the basis of the drive amounts, wherein, when judging that the fine work manipulator is to reach the operating range when the fine work manipulator is caused to operate up to the tip position of the fine work manipulator by the fine work manipulator alone, the control device calculates the drive amounts of the fine work manipulator and the robot unit, with the operating position being the target position, and controls operations of the fine work manipulator and the robot unit on the basis of the drive amounts.

2. The device for fine work according to claim 1, wherein when the control device calculates the drive amounts of the fine work manipulator and the robot unit the operating range of the fine work manipulator is not exceeded, and controls operations of the fine work manipulator and the robot unit on the basis of the drive amounts.

3. The device for fine work according to claim 1, wherein, when judging that the fine work manipulator is to reach the operating range when the fine work manipulator is caused to operate up to the tip position of the fine work manipulator by the fine work manipulator alone, the control device calculates the drive amounts of the fine work manipulator and the robot unit so as to cause the fine work manipulator to operate to within the operating range, and also cause the robot unit to move the fine work manipulator to the operating position, and controls operations of the fine work manipulator and the robot unit on the basis of the drive amounts.

4. The device for fine work according to claim 1, wherein the control device holds a threshold value of the fine work manipulator with respect to the operating range, and upon judging that the fine work manipulator is to reach the threshold value, judges that the operating range is to be reached.

5. The device for fine work according to claim 1, wherein the fine work manipulator includes a parallel link mechanism of a plurality of degrees of freedom that is three or more degrees of freedom, the parallel link mechanism having: a base that is supported at a predetermined location in a space in which the object of work is present; an end effector that handles the object of work or working equipment; and a plurality of links disposed in parallel between the base and the end effector, a position and an orientation of the end effector being variable with respect to the base within a predetermined range, and the parallel link mechanism causes linear movement of one end portion of each of the links by a plurality of linear actuators supported by the base, thereby moving the end effector linked to another end portion of each of the links.

6. The device for fine work according to claim 5, wherein the parallel link mechanism has an initial position that is a symmetrical position with respect to a center axis of the fine work manipulator, and when judging that the fine work manipulator is to reach the operating range, the control device calculates the drive amount of the fine work manipulator so as to cause the parallel link mechanism to move to the initial position, and also calculates the drive amount of the robot unit so that the tip position of the fine work manipulator at that point in time does not move.

7. The device for fine work according to claim 5, wherein the parallel link mechanism is a mechanism of six degrees of freedom or more, in which six or more of the linear actuators and the links are disposed in parallel.

8. The device for fine work according to claim 5, wherein the linear actuators are moving coil linear motors in which a coil is part of a moving element, and also a permanent magnet is part of a stationary element, the moving element has a linear-motion slider that is attached so as to be capable of linear movement with respect to the base, and the coil that is cylindrical and that is integrally attached to the linear-motion slider, with the coil being disposed in an orientation in which an axial direction of the coil is parallel to a direction of movement of the linear-motion slider, and the stationary element has the permanent magnet that is cylindrical and is shorter than the coil, the permanent magnet is disposed in a state in which a cylindrical axial direction thereof matches that of the coil, and the coil movably passes through a space portion inside the cylinder of the permanent magnet.

9. The device for fine work according to claim 8, wherein moving directions of each of the moving elements of the linear motors are parallel to each other, and also the permanent magnets are disposed arrayed about a predetermined imaginary center line that is parallel to the movement directions of the moving elements such that the permanent magnets are on a side closest to the imaginary center line.

10. The device for fine work according to claim 1, wherein the robot unit has, at a tip thereof, the fine work manipulator attached thereto, and supports this fine work manipulator with three rotational degrees of freedom and one translation degree of freedom in a radial direction.

11. A device for fine work executing a predetermined operation relating to fine work with respect to an object of work, in place of a person, wherein the device for fine work has a fine work manipulator that is configured to perform the fine work and that has a predetermined operating range, a robot unit that is configured to support the fine work manipulator and that has a wider operating range than the operating range of the fine work manipulator, and a control device that is configured to control driving of the fine work manipulator and the robot unit, and the control device accepts input of movement of a tip position of the fine work manipulator, which is an operating position of the fine work, and, with the operating position being a target position, calculates drive amounts of the fine work manipulator and the robot unit, and controls operation of the fine work manipulator and the robot unit on the basis of the drive amounts, wherein the fine work manipulator includes a parallel link mechanism of a plurality of degrees of freedom that is three or more degrees of freedom, the parallel link mechanism having: a base that is supported at a predetermined location in a space in which the object of work is present; an end effector that handles the object of work or working equipment; and a plurality of links disposed in parallel between the base and the end effector, a position and an orientation of the end effector being variable with respect to the base within a predetermined range, the parallel link mechanism causes linear movement of one end portion of each of the links by a plurality of linear actuators supported by the base, thereby moving the end effector linked to another end portion of each of the links the parallel link mechanism has an initial position that is a symmetrical position with respect to a center axis of the fine work manipulator, and when judging that the fine work manipulator is to reach the operating range, the control device calculates the drive amount of the fine work manipulator so as to cause the parallel link mechanism to move to the initial position, and also calculates the drive amount of the robot unit so that the tip position of the fine work manipulator at that point in time does not move.

12. The device for fine work according to claim 11, wherein the control device holds a threshold value of the fine work manipulator with respect to the operating range, and upon judging that the fine work manipulator is to reach the threshold value, judges that the operating range is to be reached.

13. The device for fine work according to claim 11, wherein the robot unit has, at a tip thereof, the fine work manipulator attached thereto, and supports this fine work manipulator with three rotational degrees of freedom and one translation degree of freedom in a radial direction.

14. The device for fine work according to claim 11, wherein the parallel link mechanism is a mechanism of six degrees of freedom or more, in which six or more of the linear actuators and the links are disposed in parallel.

15. The device for fine work according to claim 11, wherein the linear actuators are moving coil linear motors in which a coil is part of a moving element, and also a permanent magnet is part of a stationary element, the moving element has a linear-motion slider that is attached so as to be capable of linear movement with respect to the base, and the coil that is cylindrical and that is integrally attached to the linear-motion slider, with the coil being disposed in an orientation in which an axial direction of the coil is parallel to a direction of movement of the linear-motion slider, and the stationary element has the permanent magnet that is cylindrical and is shorter than the coil, the permanent magnet is disposed in a state in which a cylindrical axial direction thereof matches that of the coil, and the coil movably passes through a space portion inside the cylinder of the permanent magnet.

16. The device for fine work according to claim 15, wherein moving directions of each of the moving elements of the linear motors are parallel to each other, and also the permanent magnets are disposed arrayed about a predetermined imaginary center line that is parallel to the movement directions of the moving elements such that the permanent magnets are on a side closest to the imaginary center line.

* * * * *